United States Patent [19]

Magre et al.

[11] Patent Number: 4,935,012
[45] Date of Patent: Jun. 19, 1990

[54] SAFETY DEVICE FOR MEDICAL NEEDLES

[75] Inventors: George R. Magre; Maria L. Magre, both of 2517 Via Olvera, Palos Verdes Estates, Calif. 90274; Paul Greskovics, Manhattan Beach, Calif.

[73] Assignees: George R. Magre; Maria Linda Magre, both of Palos Verdes Estates, Calif.

[21] Appl. No.: 205,309

[22] Filed: Jun. 10, 1988

[51] Int. Cl.$^5$ ............................................. A61M 5/32
[52] U.S. Cl. ................................. 604/192; 604/263
[58] Field of Search ............... 604/110, 192, 197, 198, 604/263

[56] References Cited

U.S. PATENT DOCUMENTS

| | | | |
|---|---|---|---|
| 2,571,653 | 10/1951 | Bastien | 604/198 |
| 2,847,995 | 8/1954 | Adams | 604/198 |
| 2,876,770 | 3/1959 | White | 604/198 |
| 4,148,316 | 4/1979 | Xanthopoulos | 604/192 |
| 4,425,120 | 1/1984 | Sampson et al. | 604/198 |
| 4,573,976 | 3/1986 | Sampson et al. | 604/198 |
| 4,631,057 | 12/1986 | Mitchell | 604/198 |
| 4,664,654 | 5/1987 | Strauss | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |
| 4,723,943 | 2/1988 | Spencer | 604/198 |
| 4,725,267 | 2/1988 | Vaillancourt | 604/192 |
| 4,735,618 | 4/1988 | Hagen | 604/192 |
| 4,737,144 | 4/1988 | Choksi | 604/198 |
| 4,778,453 | 10/1988 | Lopez | 604/198 |
| 4,804,371 | 2/1989 | Vaillancourt | 604/263 |
| 4,804,372 | 2/1989 | Laico et al. | 604/263 |
| 4,832,696 | 5/1989 | Luther et al. | 604/198 |
| 4,842,586 | 6/1989 | Hogan | 604/198 |

FOREIGN PATENT DOCUMENTS

| | | |
|---|---|---|
| 949836 | 6/1974 | Canada . |
| 0286992 | 10/1988 | European Pat. Off. ............ 604/192 |
| 2079607 | 1/1982 | United Kingdom ................ 604/198 |
| 89/00865 | 2/1989 | World Int. Prop. O. .......... 604/192 |

*Primary Examiner*—Stephen C. Pellegrino
*Assistant Examiner*—Sharon Rose
*Attorney, Agent, or Firm*—Kelly, Bauersfeld & Lowry

[57] ABSTRACT

An improved safety device is provided for protecting medical personnel and the like against needle stick injuries and/or exposure to communicable diseases or other harmful agents. The safety device comprises an elongated protective sleeve supported by front and rear bearing members for sliding movement about a medical needle and its associated support structure, such as a support hub or barrel. The protective sleeve is slidable in a stable manner from a first position with the pointed end of the needle safely retracted within and shielded by the front bearing member to a second position with the needle projecting through and beyond the front bearing member for normal use. After use, the sleeve is slidable to a third position derailing the pointed needle end from the front bearing member, and exposing a visual indicator to indicate that the needle has been used. Closure flaps associated with the front bearing member positively prevent needle reinsertion through the front bearing member, and thereby prevent accidental or unauthorized needle re-use. Detent members interacting between the rear bearing member and the needle support structure releasably lock the protective sleeve in the various positions.

24 Claims, 5 Drawing Sheets

SAFETY DEVICE FOR MEDICAL NEEDLES

BACKGROUND OF THE INVENTION

This invention relates generally to protective devices for use with medical needles and the like to safeguard against accidental and/or unauthorized needle use. More particularly, this invention relates to an improved yet relatively simple and economical safety device for protecting medical personnel and the like against accidental contact with medical needles and/or exposure to potentially hazardous patient fluids thereon in the course of normal needle handling and use. Moreover, this invention relates to a simplified and reliable locking arrangement for preventing accidental or unauthorized re-use of a used medical needle.

Medical needles are widely used by the health care industry in the course of patient diagnosis and/or treatment. Such medical needles commonly comprise an elongated hollow metal tube mounted within and protruding from an appropriate support structure, such as a syringe barrel, a support hub for attachment to a syringe barrel, or other structures such as fittings adapted for attachment to fluid specimen containers of the type used to obtain blood samples, etc. A forward end of the metal tube is shaped to define a sharp point adapted for transcutaneous insertion into the body of a patient for purposes of drawing patient fluids for analysis, or for injecting medication or other fluids into the patient. Modern medical needles are most commonly provided in a pre-sterilized package intended for disposal after a single use, with a removable plastic cap typically mounted onto the support structure in a position covering the needle to safeguard against accidental contact with the needle prior to use. After the medical needle is used, the cap is desirably re-installed to re-cover the needle prior to discard into a suitable waste receptacle.

The handling and use of medical needles requires extreme caution to prevent accidental needle stick injuries. More specifically, considerable attention and manual dexterity are required to avoid occasional infliction of needle injuries upon health care workers and other unintended persons. When such needle sticks occur prior to the intended use of the needle, sterility of the medical needle is compromised. Moreover, and more importantly, post-use needle sticks expose persons other than the patient to blood-borne diseases and other organisms which might be present on a used needle. For example, it is well recognized that a variety of contagious and potentially dangerous diseases such as hepatitis, acquired immune deficiency syndrome (AIDS), and others can be transmitted by contact with patient body fluids present on a used medical needle.

Moreover, in recent years, discarded medical needles have been the subject of unauthorized re-use by persons involved in illegal or illicit drug use. Prevention of such unauthorized re-use has become extremely desirable to curb the flow and use of illegal drugs, and further to prevent uncontrolled spread of communicable diseases resulting from contact with contaminated needles.

In the prior art, a variety of devices and systems have been proposed for protecting medical personnel against accidental contact with medical needles, and/or for preventing unauthorized re-use of medical needles. Some f these devices have utilized sleeve-type structures mounted about the barrel of a hypodermic syringe for extension or retraction movement about the syringe barrel for respectively covering or exposing a hypodermic needle. Such sleeve-type structures have normally included complex tab and track mechanisms for guiding the sleeve between the extended and retracted positions, with some designs intending to lock the sleeve in the extended position after needle use. However, these devices have generally exposed the needle to view and potential access through a relatively large open end of the sleeve when said sleeve is in the retracted position. See, for example, the devices described in U.S. Pat. Nos. 4,702,738; 4,631,057; 4,737,144; 4,425,120; and 4,723,943. Other protective devices have envisioned needle guards With narrow apertures for passage of a medical needle during normal use, after which the guard is displaced beyond the needle point and manipulated to a position intended to minimize the chances of needle reinsertion through the guard aperture. See, for example, U.S. Pat. Nos. 4,725,267 and 4,735,618. However, this latter group of devices has been characterized by relatively complex mechanical arrangements which have not positively locked the medical needle against access or reuse.

There exists, therefore, a significant need for further improvements in protective devices and systems for preventing accidental and/or unauthorized contact with medical needles, particularly with respect to the provision of a simple, economical, and easy-to-use device which minimizes the risk of accidental needle stick injuries while additionally rendering a medical needle substantially inaccessible after use. The present invention fulfills these needs and provides further related advantages.

SUMMARY OF THE INVENTION

In accordance with the invention, a needle safety device is provided for protecting medical personnel and the like against accidental exposure to and/or contact with a medical needle, such as a needle used for drawing blood or other patient fluid, hypodermic needles, catheters, etc. The safety device comprises a relatively simple, economical and easily operated protective sleeve movable from an initial position shielding the needle point against accidental contact, to a retracted position exposing the needle for normal use, followed in turn by movement to a security or safety position shielding the needle from view and substantially preventing needle access or re-use.

In one preferred form of the invention, the protective sleeve has an elongated hollow geometry with front and rear bearing members adapted for respectively and slidably supporting the sleeve relative to the medical needle and a support structure for the needle, such as a support hub or support barrel of the type commonly used with disposable medical needles. The front bearing member defines a narrow port or aperture for close sliding reception of the needle, whereas the rear bearing member includes detent means for interacting with a complemental detent means on the support structure to releasably lock the protective sleeve in place. Closure flaps such as molding flash are included adjacent the front bearing member to positively prevent needle reinsertion through the port after withdrawal therefrom.

In a first or shipping position, the detent means locks the protective sleeve in a position with the pointed needle end seated within the front bearing member, but otherwise retracted from the forwardmost end of the sleeve to prevent human contact therewith. The protective sleeve is movable to a normal use position by sliding the sleeve rearwardly to expose the pointed needle end and a substantial portion of the needle at the forward end of the sleeve. The detent means releasably locks the sleeve in this extended position to avoid interference with normal handling and use in the course of medical procedures.

After use, the protective sleeve is movable forwardly to a third position with the pointed needle end withdrawn or derailed from the front bearing member. In this third or security position, the front bearing member is disposed axially beyond the needle such that the protective sleeve is retained on the support structure by the rear bearing member. However, the derailment of the front bearing member results in sufficient sleeve instability that the port in the front bearing member becomes misaligned with the needle point. Reinsertion of the needle point through the bearing member port for needle re-use is difficult or substantially impossible. The likelihood of needle reinsertion is further reduced by the closure flaps adjacent the bearing member port, wherein such flaps close the port upon needle derailment therefrom. A visual indicator such as a colored band on the support structure is exposed when the sleeve is in the security position to indicate that the needle has been used.

The invention is adaptable for use with different types of medical needles used throughout the health care industry. For example, the protective sleeve may be used with conventional hypodermic needles, butterfly catheters, and the like. For needle support structures adapted to thread onto other housing components, a noncircular support structure cross section may be provided for driving fit with a protective sleeve of similar noncircular cross section, thereby permitting facilitated mounting upon grasping and rotating the sleeve. Moreover, in one preferred form, the invention is adapted for use with needles used in standardized blood sample kits, wherein such needles have a double-ended construction with a front end for insertion into the patient and a rear end for insertion through a cap of a specimen collection container. In such blood sample kits, a pair of protective sleeves are provided for shielding the opposite pointed ends of the needle. For normal use, the protective sleeves interfit telescopically to expose the pointed front and rear needle ends, after which the sleeves are returnable to locked positions substantially blocking the needle ends against further access.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
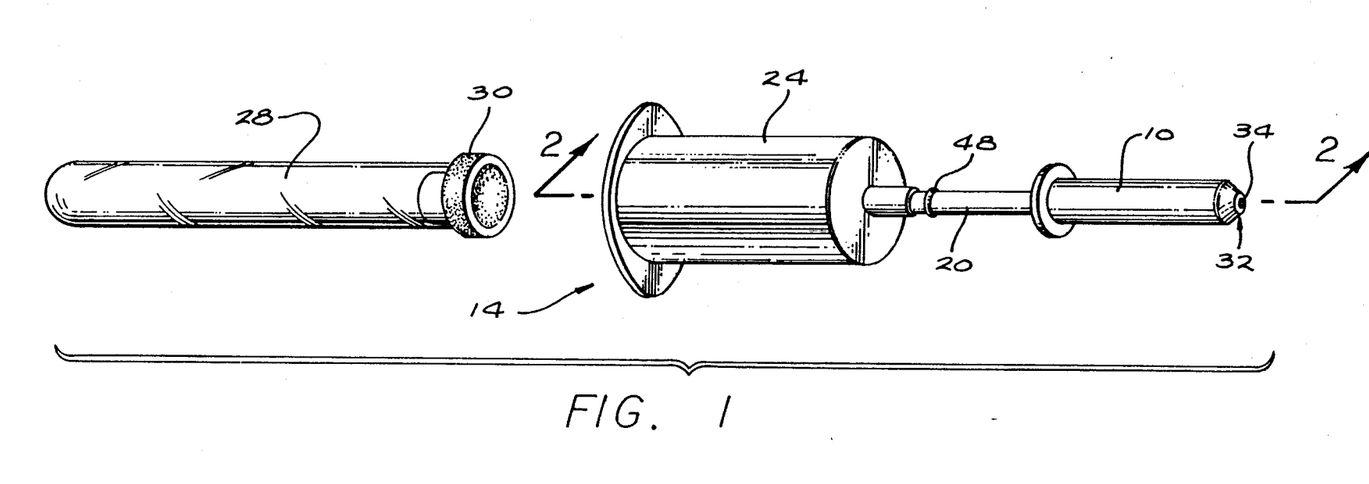
FIG. 1 is an exploded perspective view illustrating a blood sample kit incorporating a medical needle safety device embodying the novel features of the invention, and depicting a protective sleeve in a first or shipping position shielding a medical needle.
Figure 2:
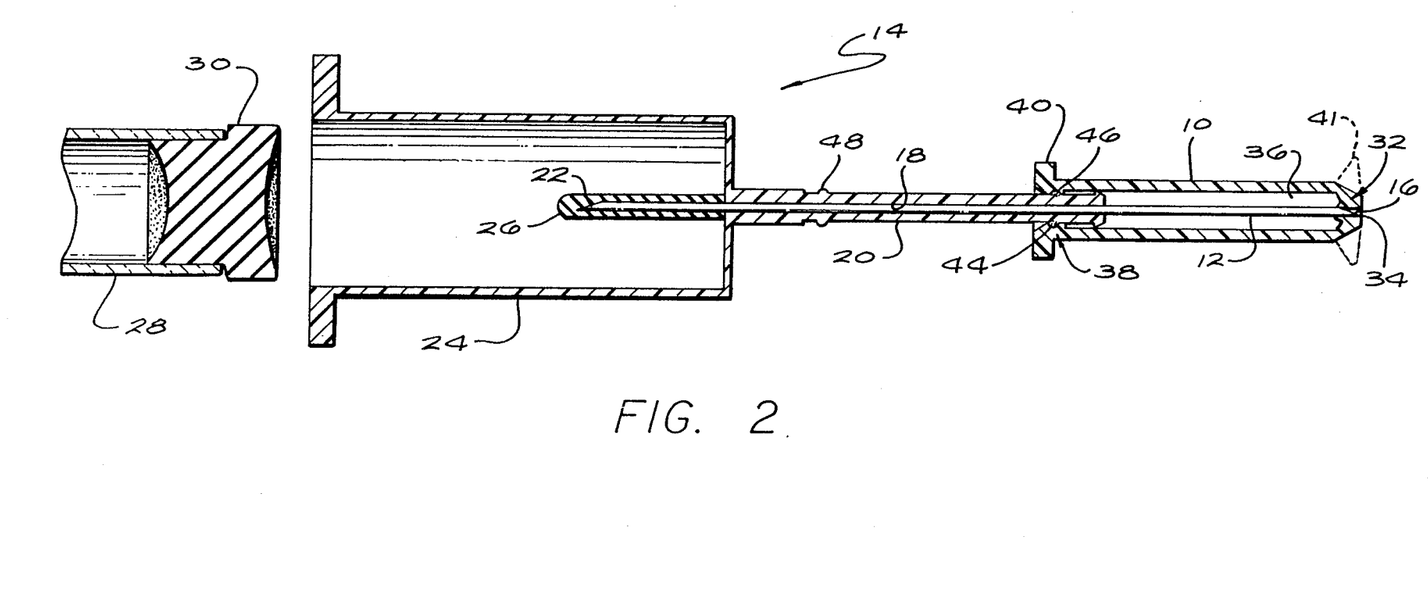
FIG. 2 is a fragmented vertical sectional view taken generally on the line 2—2 of FIG. 1.

As shown in the exemplary drawings, an improved safety device for medical needles is provided for safeguarding against undesired needle stick injuries and/or potentially dangerous contamination resulting from contact with used medical needles. The needle safety device comprises a relatively simple and easily manipulated protective sleeve referred to generally in FIG. 1 by the reference numeral 10 for preventing accidental contact with a medical needle 12 (FIG. 2). The protective sleeve 10 is movable quickly and easily to expose the medical needle 12 for normal use, after which the sleeve is movable again to a safety or security position substantially concealing and locking the needle against access or re-use. Accordingly, the protective sleeve 10 provides the important functions of safeguarding against unintended needle stick injuries, preventing human contact with potentially hazardous or contagious organisms on a used needle, and further preventing unauthorized needle re-use, for example, by users of illegal or illicit drugs.

Figure 3:
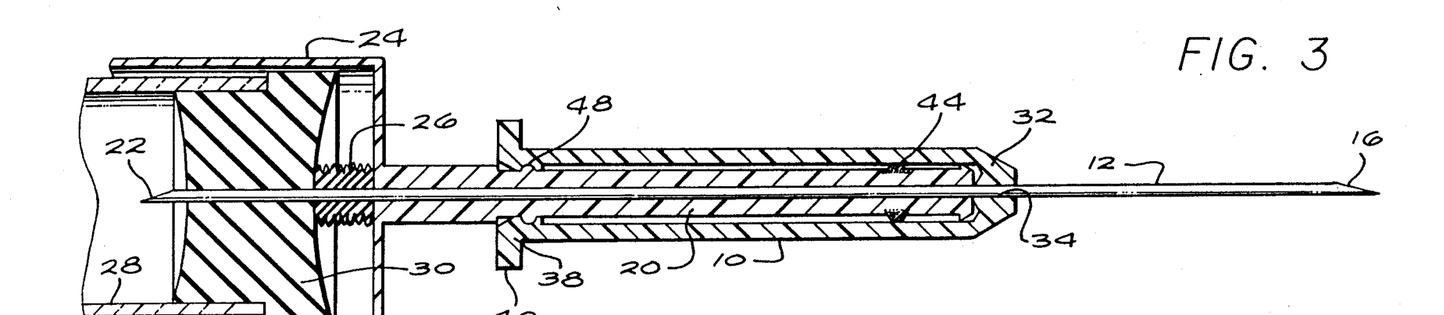
FIG. 3 is a fragmented vertical sectional view similar to FIG. 2, but depicting the protective sleeve in a second position exposing a medical needle for normal use.
Figure 4:
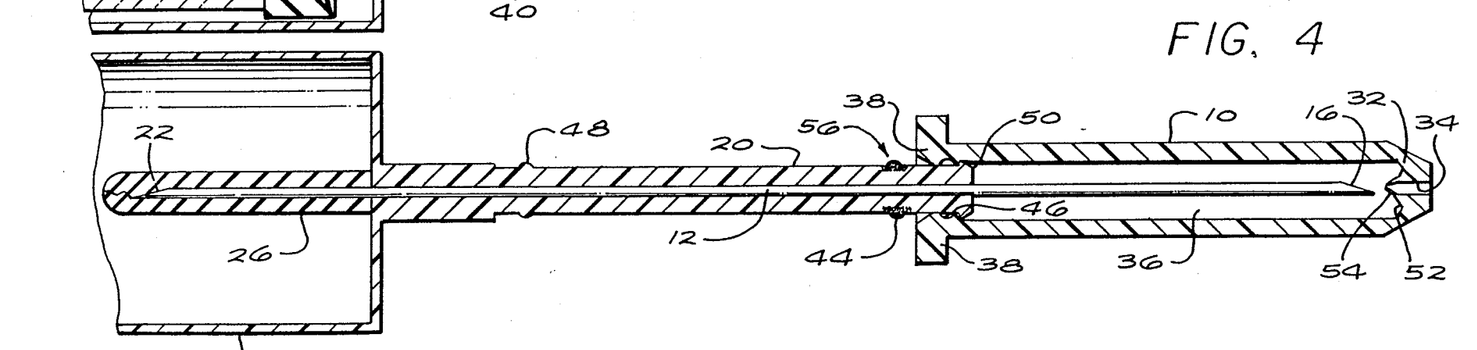
FIG. 4 is a fragmented vertical sectional view similar to FIGS. 2 and 3, but showing the protective sleeve displaced to a third position shielding and locking the medical needle from view or access.

FIGS. 1-4 illustrate the needle safety device of the present invention for use in combination with a blood sample kit 14 adapted for use in drawing a sample of patient blood or other body fluid for analysis. In this exemplary form of the invention, the medical needle 12 has a hollow double-ended configuration with a forward pointed end 16 for transcutaneous insertion into a patient (not shown), typically by intravenous insertion for drawing a blood sample. As shown in FIGS. 2-4, the double ended needle 12 is securely mounted within a small bore 18 of a suitable support hub or structure, such as a generally cylindrical support barrel 20 formed preferably from a lightweight molded plastic material or the like. Alternately, the exterior of the barrel 20 may be provided with a noncircular cross sectional shape for easy manual grasping, if desired. The needle 12 protrudes forwardly a substantial distance from the support barrel 20 and terminates in the pointed forward end 16, whereas the opposite end of the needle protrudes rearwardly from the support barrel and terminates in a pointed rear end 22.

The needle support barrel 20 is joined at its rear end, preferably by integral molding, to a generally cylindrical and rearwardly open housing member 24 of larger diametric size. The protruding rear end 22 of the medical needle 12 is disposed within the hollow interior of this housing member 24, with the length of the needle being selected such that the pointed rear end 22 is recessed from the open end of the housing member 24 in a position substantially protected against access. An elastomer sheath 26 of the type described in Canadian Patent No. 949,836 is seated over this pointed rear end 22 of the needle for maintaining a sterilized condition and for controlling fluid flows during use, as will be described. A specimen container 28 such as an evacuated tube closed by an elastomeric self-sealing stopper cap 30 is receivable end-first into the housing member 24 for receiving a blood sample or the like drawn through the medical needle 12. The entire product may, of course, be prepackaged in one or more units in a sterilized condition ready for use.

The protective sleeve 10 comprises an elongated tubular structure mounted generally about the medical needle 12 and the associated support barrel 20 for sliding movement. More particularly, as shown in FIGS. 1 and 2, the protective sleeve 10 is shaped to define a front bearing member 32 formed with a narrow port or aperture 34 sized for relatively close sliding reception of the medical needle 12. This port 34 opens into an interior sleeve chamber 36 of comparatively larger diameter such that the major portion of the protective sleeve 10 is radially spaced from the outer diameter surfaces of the needle 12. Accordingly, when the needle 12 is received through the bearing member port 34, the front bearing member 32 provides a single contact point for sliding support of the protective sleeve 10 relative to the medical needle 12.

The opposite or rear end of the protective sleeve 10 includes a second or rear bearing member 38 having a diametric size smaller than the sleeve chamber 36. This rear bearing member 38 is sized for relatively close sliding displacement along the exterior of the support barrel 20, and thereby provides a second contact point for sliding support of the sleeve 10 with respect to the needle 12. The front and rear bearing members therefore cooperate to provide a pair of longitudinally spaced support points for permitting smooth and stable sleeve sliding motion relative to the needle 12 and barrel 20. Conveniently, a radially enlarged flange 40 is located at or near the rear end of the sleeve 10 for facilitated manual grasping of the sleeve throughout displacement to the various operational positions. As depicted in dotted lines in FIG. 2, an additional radially enlarged flange 41 may be provided at the forward sleeve end to facilitate manual grasping, if desired.

FIG. 2 illustrates the kit 14 with the protective sleeve 10 oriented in a first or shipping position substantially concealing and shielding the medical needle 12. More specifically, in this shipping position, the pointed forward end 16 of the needle 12 is received partially into the port 34 in the front bearing member 32. A removable cap (not shown) may be mounted over the end of the protective sleeve 10 to insure against accidental needle contact as the kit is removed, for example, from associated packaging (not shown) and prepared for use in drawing a blood sample or the like. A detent member such as a raised detent rib 44 on the support barrel 20 is received into an annular detent recess 46 within the rear bearing member 38 to releasably lock the protective sleeve 10 in the shipping position.

The kit 14 is prepared for use in drawing a blood sample or the like by retracting the protective sleeve 10 along the needle 12 and the associated support barrel 20 to expose a substantial portion of the needle 12 for normal use. Such retraction is illustrated in FIG. 3 to expose the pointed forward end 16 of the needle and a sufficient portion of the needle shank for conventional transcutaneous insertion into the body of a patient. The front bearing member 32 and the rear bearing member 38 cooperatively support the sleeve 10 for relatively stable, longitudinally sliding motion relative to the needle and the support barrel, respectively. A rear detent rib 48 near a rear end of the support barrel 20 releasably locks into the detent recess 46 for releasably holding the sleeve 10 in the retracted position with the needle exposed for normal use. Conveniently, upon initial insertion of the needle into the patient, patient fluids are prevented from passage through the needle by the elastomeric sheath 26 which closes the rear end of the needle against fluid flow.

Following insertion of the needle into the patient, the specimen container 28 is advanced into the open end of the housing member 24 to engage the stopper cap 30 with the pointed rear end 22 of the medical needle 12. Upon such engagement, the needle 12 pierces the elastomeric sheath 26 and the stopper cap 30 to provide an open flow path through the needle from the patient to the interior of the container 28. As is known in the art, the container 28 is desirably evacuated for drawing of the body fluids into the container. The sheath 26 collapses (FIG. 3) to accommodate piercing of the stopper cap 30, after which the container 28 may be removed from the needle as the sheath 26 returns resiliently to a position closing and sealing the rear end 22 of the needle (FIG. 4). The general construction and operation of the elastomeric sheath 26 in conjunction with the piercible stopper cap of the collection container 28 are described in further detail, for example, in Canadian Patent No. 949,836, which is incorporated by reference herein.

After the sample is drawn and the needle 12 withdrawn from the patient, the protective sleeve 10 is moved quickly and easily to a security or safety position denying further access to the now-used needle 12. More particularly, with reference to FIG. 4, the sleeve 10 is slidable longitudinally in an opposite or forward direction along the needle 12 and the associated support barrel 20 to displace the front bearing member 32 to a position forward or beyond the pointed forward end 16 of the needle. Alternately stated, the front bearing member 32 is displaced to a position derailing the pointed needle end 16 from the bearing member port 34, thereby positioning the pointed end 16 inboard relative to the front bearing member 32 at a location within the sleeve chamber 36. To achieve this derailed condition, the rear bearing member 38 is displaced forwardly to a position beyond the forward detent rib 44 and into axial abutment with a raised land 50 at the forwardmost end of the support barrel 20.

When such derailment occurs, the protective sleeve 10 is no longer supported in a stable manner by two spaced contact points relative to the needle and support barrel. Instead, the sleeve 10 is supported entirely by the rear bearing member 38 which results in relative instability at the front bearing member 32 such that misalignment between the pointed needle end 16 and the port 34 tends to occur. With such misalignment, accidental or attempted manipulation of the sleeve 10 for needle reinsertion into or through the port 34 is rendered difficult or substantially impossible. The difficulty of such needle insertion is enhanced by forming the inboard face of the front bearing member 32 with an axially presented annular recess 52 surrounding the port 34, whereby attempts to reinsert the needle point 16 tend to guide the needle toward misaligned seating within the recess 52. Moreover, needle reinsertion into the port 34 is further prohibited by axially inboard angled closure flaps 54 which resiliently close upon needle derailment to positively close the port. Such closure flaps 54 may conveniently comprise intentional molding flash allowed to remain in the course of manufacturing the sleeve 10 from lightweight molded plastic or the like.

In accordance with further aspects of the invention, the support barrel 20 includes means for visually indicating placement of the protective sleeve 10 in the security or safety position after needle use. Such visual indication, in the preferred form, comprises colored indicia such as a colored band 56 encircling the support barrel at or near the forward detent rib 44. When this colored band 56 is exposed to view, positive indication is provided that the needle has already been used, or is otherwise rendered unusable by derailment of the needle point 16 from the front bearing member 32.

Figure 5:
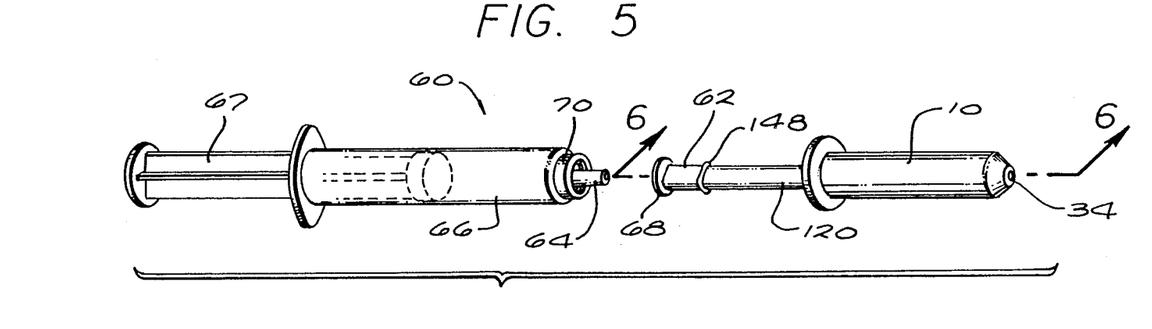
FIG. 5 is an exploded perspective view illustrating a hypodermic syringe incorporating the safety device of the present invention, and showing a protective sleeve in a first or shipping position.
Figures 6, 7:
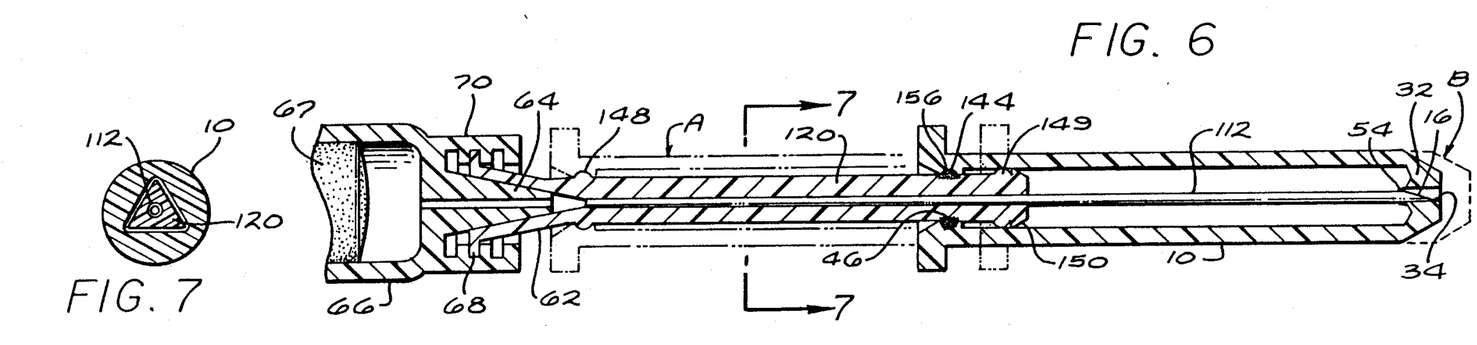
FIG. 6 is a fragmented vertical sectional view taken generally on the line 6—6 of FIG. 5.
FIG. 7 is a sectional view taken generally on the line 7—7 of FIG. 6.

FIGS. 5 and 6 depict one alternative preferred form of the invention wherein the needle safety device system is adapted for use with a hypodermic syringe 60. In this form of the invention, a protective sleeve 10 generally conforming to the sleeve described above with respect to FIGS. 1–4 is mounted about a modified support hub or barrel 120. The support barrel 120 supports a standard single-ended hypodermic needle 112 having a forwardly protruding, pointed forward end 116. A rear end of the support barrel 120 is joined preferably by integral molding with an attachment cuff 62 of standardized construction. This cuff 62 has a rearwardly expanding, truncated conical shape adapted for press-fit attachment onto a conical nose 64 of a standard syringe housing 66. Alternately, or in addition, the cuff 62 may include a radially enlarged rear flange 68 for threading into an internally threaded nose fitting 70 of the syringe housing 66. FIGS. 5 and 6 depict a combination of this press-fit and threaded geometry, although either form of syringe attachment may be omitted depending upon the type and style of syringe used. The exterior of the support barrel 120 is conveniently provided with a noncircular cross sectional configuration for driven rotational engagement by a complemental inner cross sectional geometry of the sleeve, as viewed in FIG. 7, to facilitate threaded engagement with the cuff 62 by rotation of the sleeve 10.

In use, the protective sleeve 10 is displaced longitudinally on the support barrel 120 and associated needle 112 in generally the same manner as described with respect to FIGS. 1–4. More particularly, as shown in solid lines in FIGS. 5 and 6, the protective sleeve 10 is initially placed in a shipping position with the pointed needle end 116 seated partially within a narrow port 34 of a front bearing member 32. Detent members interacting between the support barrel 120 and a rear bearing member 38 on the protective sleeve 10, such as a barrel rib 144 and a sleeve recess 46, cooperatively retain the protective sleeve 10 in the shipping position. When use is desired, the protective sleeve 10 is slidable rearwardly to expose the needle 112 for normal use, with the detent recess 46 receiving a rear barrel rib 148 to releasably lock the sleeve in the retracted position. This retracted position of the sleeve is depicted by the dotted lines A in FIG. 6. After use, the protective sleeve 10 is slidable forwardly to derail the needle 112 from the front bearing member 32 in the same manner as previously described. A colored band 156 or the like is conveniently provided at or near the detent rib 144 for visibility when the sleeve is displaced to the security or safety position. If desired, an additional detent rib 149 may be provided in combination with a forward land 150 for locking the sleeve 10 in the safety or security position, as depicted by the dotted lines B in FIG. 6.

FIGS. 8–11 show still another alternative preferred embodiment of the invention. In this version, the safety device is adapted for use with a double-ended needle 12 of the type described generally with respect to FIGS. 1–4 for use in drawing blood samples and the like. In this version, however, a modified support barrel 220 is provided for removable threaded connection into a nose fitting 72 of an open-ended housing member 224 which is adapted in turn for receiving a specimen container 28 (FIG. 1). Means are provided in this embodiment for shielding both ends of the medical needle against access.

Figures 8, 9, 10:
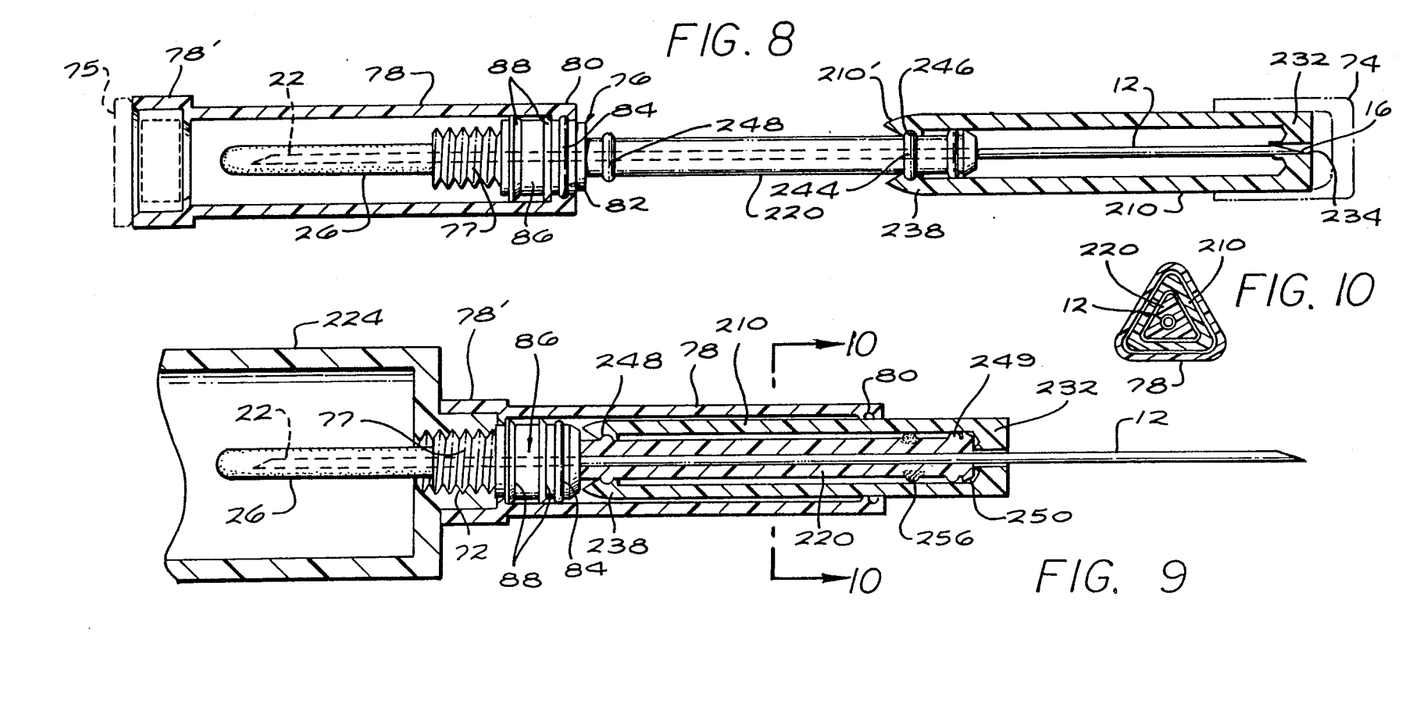
FIG. 8 is a fragmented vertical sectional view similar to FIG. 4, but depicting still another embodiment of the invention including a pair of telescopic protective sleeves for use with a double ended medical needle.
FIG. 9 is a fragmented vertical sectional view similar to FIG. 8, but depicting the protective sleeves telescoped to retracted positions exposing the double ended needle for use.
FIG. 10 is a vertical sectional view taken on the line 10—10 of FIG. 9.

More specifically, a protective front sleeve 210 includes a front bearing member 232 with a small port 234 therein, and a rear bearing member 238. The front and rear bearing members 232 and 238 are slidably positioned relative to a projecting forward end of the needle 12 and the support barrel 220, respectively. In an initial shipping position, the pointed forward end 16 of the needle is received but shielded within the bearing member port 234, wherein a detent recess 246 at the rear bearing member 238 releasably receives and locks with a detent rib 244. A removable cap 74 may be provided over the forward end of the sleeve 220 in the shipping configuration.

The rearward end of the support barrel 220 includes a mounting fitting 77 having a rearwardly projecting male threaded member 78 sized for thread-in attachment to the nose fitting 72 on the housing member 224. The rear end of the needle 12 projects through this fitting 76 and terminates in the pointed rear end 22 which is concealed within an elastomerio sheath 26, as previously described. In the initial shipping configuration, prior to attachment of the housing member 224, a protective rear sleeve 78 projects rearwardly about the pointed needle end 22 to protect the needle against undesired contact or access. A forward bearing member 80 on the rear sleeve 78 includes a detent recess 82 for releasably locking with a detent rib 84 on the fitting 76 to secure the rear sleeve in the shipping position (FIG. 8). A rear cap 75 may also be provided to close the rear sleeve 78 in the shipping configuration.

When use of the double-ended needle 12 is desired, the male threaded member 77 is threaded into the nose fitting 72 of the housing member 224. Such thread-in mounting is facilitated by forming the barrel 220 and sleeve 210 with mating noncircular geometries (FIG. 10), thereby permitting sleeve rotation to correspondingly rotate the member 77 into the nose fitting. The protective front sleeve 210 is then displaced rearwardly to expose the pointed forward end 16 for normal use. In this position, as depicted in FIG. 9, the front and rear bearing members 232 and 238 guide the sleeve 210 smoothly to a retracted position with the detent recess 246 engaging a second detent rib 248 on the support barrel 220. The protective rear sleeve 78 is then displaced forwardly in concentric relation about the front sleeve 210 to expose the pointed rear end 22 of the needle for normal use. This forward sliding motion may be performed by manually grasping and moving the rear sleeve 78, or by pressing the nose fitting 72 on the housing member 224 into an expanded rear end 78, of the rear sleeve 78. The bearing member 80 on the rear sleeve 78 provides smooth sliding support by engagement with the outer diameter of the front sleeve 210, as the two sleeves 78 and 210 are placed into a collapsed or telescoped geometry. A curvedly tapered rear end 210, on the front sleeve 210 conveniently facilitates transition of the rear sleeve bearing member 80 from the fitting 76 onto the front sleeve 210.

The protective rear sleeve 78 thus accommodates threaded attachment of the housing member 224 with the support barrel fitting 76 for normal use of the needle 12 in drawing a blood sample or the like. After such use, the housing member 224 is unthreaded from the support barrel fitting 76 (if desired) and disposed. Such unthreading is made possible by forming the interior of the rear sleeve 78 in a noncircular geometry for rotational interlock with the support barrel 220 and associated mounting fitting 76 (FIG. 10). When the housing member is removed, the protective rear sleeve 78 is movable rearwardly about the fitting 76 to displace the bearing member 80 beyond the detent rib 84 to a locked position seated within an annular pocket 86 located between a pair of raised lands 88. In this position, as viewed in FIG. 11, the lands 88 substantially lock the rear sleeve 78 in a position shielding the rear end 22 of the needle 16 against access. The front sleeve 210 is similarly displaced to a locked position with the forward end 16 of the needle derailed from the front bearing member 232, and with closure flaps 254 at the front bearing member positively preventing needle reinsertion or re-use. A colored band 256 located at or near the detent rib 254 may be provided to provide positive indication of needle use and locking of the protective sleeve 210. Moreover, a third detent rib 249 may be provided near the front end of the support barrel 220 in cooperation with a raised land 250 for securely holding the sleeve 210 in the locked condition.

Figure 13:
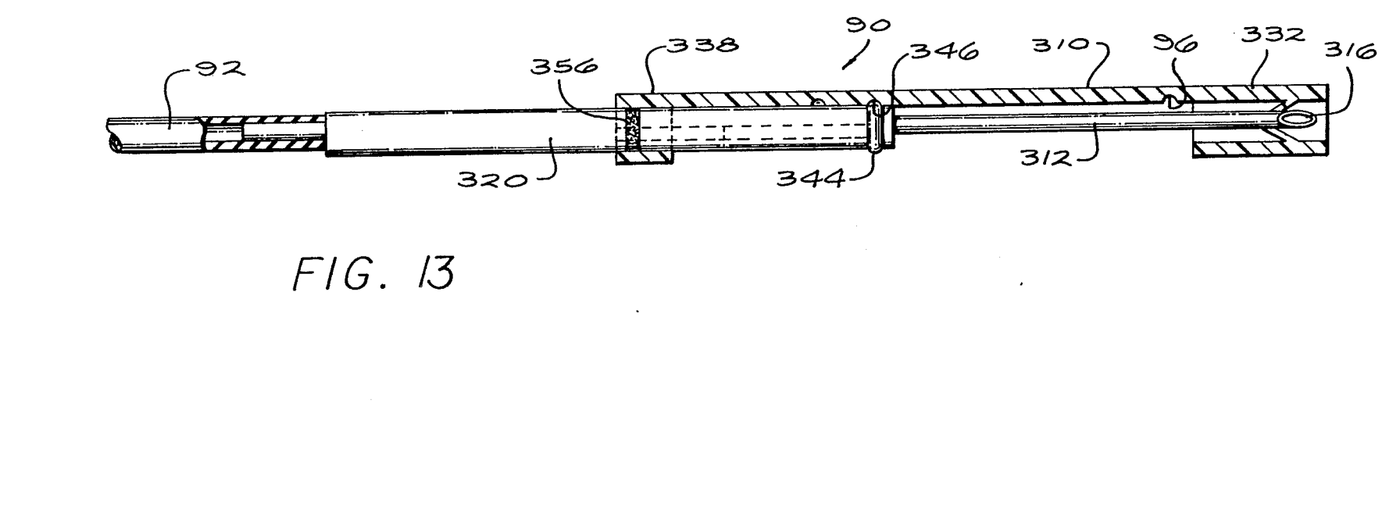
FIG. 13 is a fragmented vertical sectional view taken generally on the line 13—13 of FIG. 12.
Figure 14:
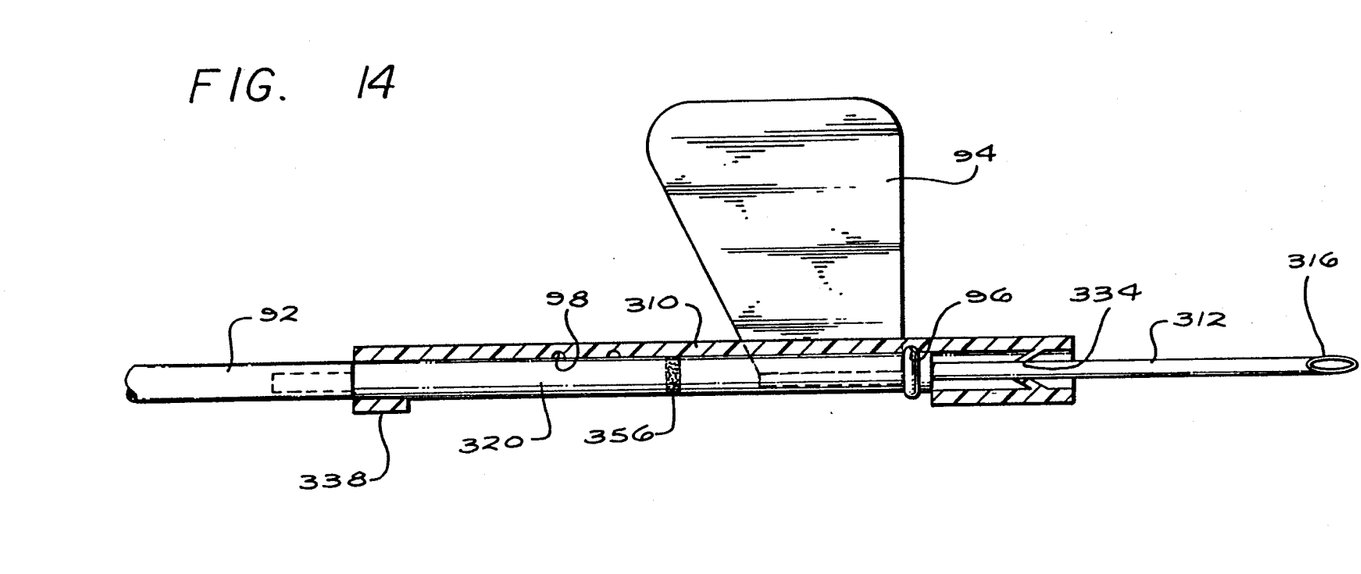
FIG. 14 is a fragmented vertical sectional view similar to FIG. 13, but depicting the protective sleeve retracted to expose a catheter needle for use.
Figure 15:
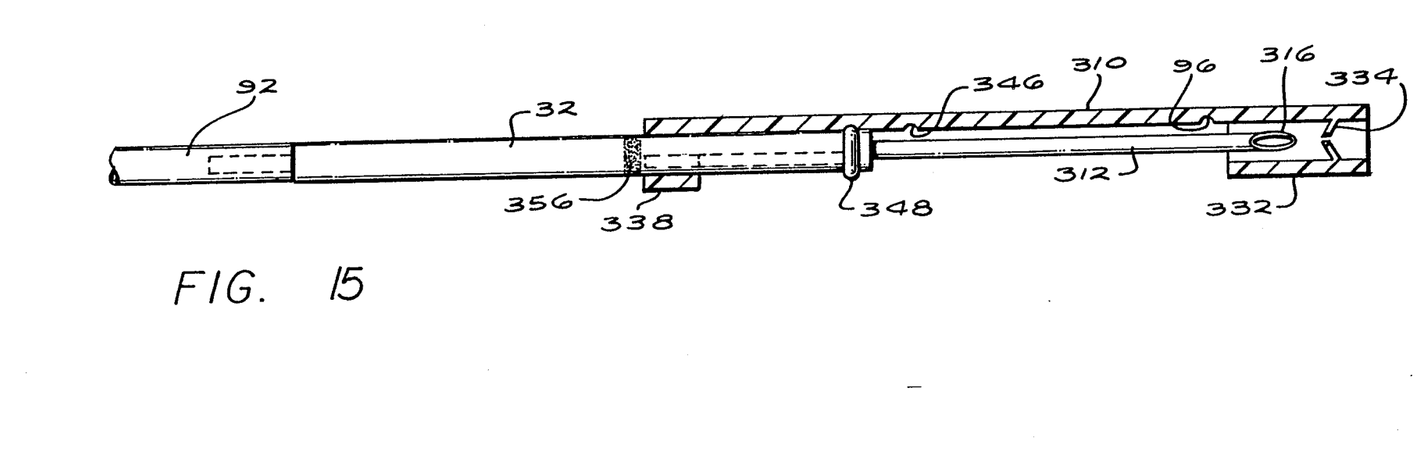
FIG. 15 is a fragmented vertical sectional view similar to FIGS. 13 and 14, but depicting the protective sleeve displaced to a security position shielding the needle.

FIGS. 12-15 show still another preferred form of the invention adapted for use in shielding and protecting a medical needle 312 of a butterfly catheter or infusion set 90 or the like. In this embodiment, the general overall construction and use of the butterfly catheter 90 is relatively standard in the art. However, the catheter 90 includes an elongated protective sleeve 310 for initially shielding the catheter needle 312 (FIGS. 12 and 13), while accommodating movement to a retracted position permitting normal use (FIG. 14) followed by movement to a locked position substantially preventing contact with or re-use of the needle (FIG. 15).

Figures 11, 12:
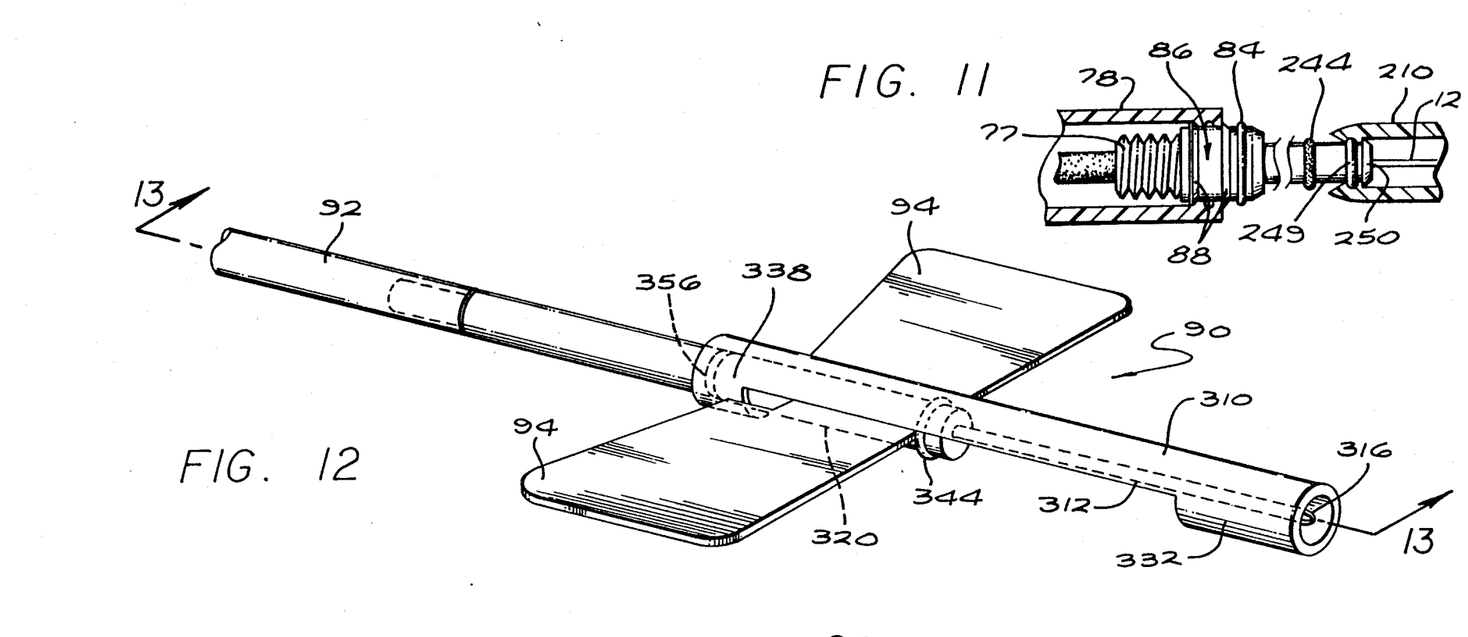
FIG. 11 is a fragmented sectional view similar to portions of FIG. 9, but illustrating portions of the device in a locked configuration.
FIG. 12 is a fragmented perspective view showing the invention adapted for use with a butterfly catheter, and depicting a protective sleeve in a first or shipping position.

The illustrative butterfly catheter includes a generally cylindrical support barrel 320 carrying a forwardly projecting catheter needle 312 having a hollow construction and a pointed forward end 316. A rear end of the support barrel is adapted for connection to a length of flexible tubing 92 or the like, such that the catheter 90 can be utilized for infusing fluids through the needle into the body of a patient. Folding butterfly-shaped wings 94 are provided at opposite sides of the support barrel 320 to facilitate manual manipulation during catheter needle insertion, after which the butterfly wings can be folded flat against the patient's skin (not shown) and attached thereto by taping or the like, all in a well-known manner.

A modified protective sleeve 310 is mounted onto the butterfly catheter 90 and includes a front bearing member 332 carried slidably about the needle 312 and a rear bearing member 338 carried slidably about the support barrel 320 at a position behind the wings 94. A generally semicircular central region of the sleeve 310 interconnects these front and rear bearing members, as viewed best in FIG. 12. In a first or shipping position, the pointed forward end 316 of the needle is retracted and shielded within the front bearing member 332. A detent rib 344 formed on the support band 320 is received into a detent recess 346 in the sleeve to releasably lock the sleeve in place.

The protective sleeve 310 is movable quickly and easily to expose the needle 312 for use by retracting the sleeve rearwardly about the needle, as viewed in FIG. 14. A second detent recess 96 on the protective sleeve receives the detent rib 344 to releasably lock the sleeve in this retracted position. At the conclusion of needle use, the sleeve 310 is returned in a forward sliding direction to derail the needle 312 from a narrow port 334 within the front bearing member 332, while containing and shielding the pointed forward end 316 generally within the front bearing member. In this position (FIG. 15), the reinsertion of the needle for passage through the port 332 is substantially impossible. Moreover, the port-forming structure is provided as closure flaps which substantially and positively close the port 332 after needle derailment to prevent reinsertion and re-use. A third detent recess 98 receives the detent rib 348 in this final position to hold the protective sleeve in place. A colored band 356 or the like is exposed behind the rear bearing member 338 to indicate the used needle status.

The needle safety device of the present invention thus provides a relatively simple yet highly versatile structure for quickly and easily locking a medical needle against access or re-use. The safety device comprises a relatively simple sleeve which initially covers the needle to prevent accidental contact therewith, but is easily retracted to expose the needle for normal use. Following use, the needle is displaced quickly and easily to a security or safety position substantially blocking needle access to prevent contact therewith or unauthorized re-use.

A variety of modifications and improvements to the improved needle protection device described herein will be apparent to those skilled in the art. Accordingly, no limitation on the invention is intended by way of the description herein, except as set forth in the appended claims.

What is claimed is:

1. A needle safety device for use in combination with a medical needle having a pointed forward end, and a support member supporting said needle to protrude forwardly therefrom, said safety device comprising:

an elongated, generally tubular protective sleeve;

means for mounting said protective sleeve for longitudinal sliding motion about said support member and said needle, said mounting means including longitudinally spaced front and rear bearing members, said front bearing member having a relatively small port formed therein for sliding passage of said needle;

said sleeve being movable relative to said support member and said needle to a first position with said needle slidably supported within said front and rear bearing members and with said pointed forward end retracted within said sleeve, a second position with said pointed forward end and a substantial portion of said needle protruding from said sleeve in an outboard direction beyond said front bearing member, and a third position with said pointed forward end retracted through and derailed from said front bearing member;

means for substantially closing said port in said front bearing member when said needle is derailed therefrom to substantially prevent reinsertion therethrough; and indicia means for visibly indicating movement of said sleeve to said third position.

2. The needle safety device of claim 1 further including means for releasably locking said sleeve with respect to said support means in said first and second positions.

3. The needle safety device of claim 2 further including means for locking said sleeve in said third position.

4. The needle safety device of claim 1 wherein said closing means comprises at least one flap disposed generally adjacent said port in said front bearing member, said flap being normally biased for substantially closing said port.

5. The needle safety device of claim 4 wherein said sleeve is formed from molded plastic, and wherein said flap comprises molding flash.

6. The needle safety device of claim 1 wherein said sleeve includes an enlarged flange generally adjacent said rear bearing member for facilitated manual grasping.

7. The needle safety device of claim 2 wherein said means comprises interacting detent members.

8. The needle safety device of claim 1 further including detent members on said sleeve and said support member formed generally adjacent said rear bearing member.

9. A needle safety device for use in combination with a medical needle having a pointed forward end, and a support member supporting said needle to protrude forwardly therefrom, said safety device comprising:

an elongated, generally tubular protective sleeve;

means for mounting said protective sleeve for longitudinal sliding motion about said support member and said needle, said mounting means including longitudinally spaced front and rear bearing members, said front bearing member having a relatively small port formed therein for sliding passage of said needle;

said sleeve being movable relative to said support member and said needle to a first position with said needle slidably supported within said front and rear bearing members and with said pointed forward end retracted within said sleeve, a second position with said pointed forward end and a substantial portion of said needle protruding from said sleeve in an outboard direction beyond said front bearing member, and a third position with said pointed forward end retracted through and derailed from said front bearing member; and means for substantially closing said port in said front bearing member when said needle is derailed therefrom to substantially prevent reinsertion therethrough;

said needle member including a pointed rear end, said pointed forward and rear ends protruding in opposite directions from said support member.

10. The needle safety device of claim 9 further including an open-ended housing member adapted for removable attachment to said support member.

11. The needle safety device of claim 9 further including an open-ended housing member joined integrally to said support member.

12. The needle safety device of claim 1 wherein said support member includes means for releasable attachment to a hypodermic syringe.

13. A needle safety device for use in combination with a medical needle having a pointed forward end, and a support member supporting said needle to protrude forwardly therefrom, said safety device comprising:

an elongated, generally tubular protective sleeve;

means for mounting said protective sleeve for longitudinal sliding motion about said support member and said needle, said mounting means including longitudinally spaced front and rear bearing members, said front bearing member having a relatively small port formed therein for sliding passage of said needle;

said sleeve being movable relative to said support member and said needle to a first position with said needle slidably supported within said front and rear bearing members and with said pointed forward end retracted within said sleeve, a second position with said pointed forward end and a substantial portion of said needle protruding from said sleeve in an outboard direction beyond said front bearing member, and a third position with said pointed forward end retracted through and derailed from said front bearing member; and means for substantially closing said port in said front bearing member when said needle is derailed therefrom to substantially prevent reinsertion therethrough;

said support member including folding wings.

14. The needle safety device of claim 9 further including an auxiliary protective sleeve carried slidably about said support member and movable to a first position disposed about and shielding said pointed rear end of said needle, a second position exposing said pointed rear end for use, and a third position reshielding said pointed rear end.

15. The needle safety device of claim 14 further including means for releasably locking said auxiliary sleeve in said first and second positions.

16. The needle safety device of claim 15 further indicating means for locking said auxiliary sleeve in said third position.

17. A needle safety device for use in combination with a medical needle having a pointed forward end, and a support member supporting said needle to protrude forwardly therefrom, said safety device comprising:

an elongated, generally tubular protective sleeve;

means for mounting said protective sleeve for longitudinal sliding motion about said support member and said needle, said mounting means including longitudinally spaced front and rear bearing members, said front bearing member having a relatively small port formed therein for sliding passage of said needle;

said sleeve being movable relative to said support member and said needle to a first position with said needle slidably supported within said front and rear bearing members and with said pointed forward end retracted within said sleeve, a second position with said pointed forward end and a substantial portion of said needle protruding from said sleeve in an outboard direction beyond said front bearing member, and a third position with said pointed forward end retracted through and derailed from said front bearing member; and means for substantially closing said port in said front bearing member when said needle is derailed therefrom to substantially prevent reinsertion therethrough;

said sleeve and said support member including matingly interfitting surfaces of noncircular cross sectional shape.

18. A needle safety device for use in combination with a medical needle having a pointed forward end, and a support member supporting said needle to protrude forwardly therefrom, said safety device comprising:

an enlongated, generally tubular protective sleeve;

means for mounting said protective sleeve for longitudinal sliding motion about said support member and said needle, said mounting means including front and rear bearing members on said sleeve, said front bearing member having a narrow port formed therein for sliding reception about said needle, and said rear bearing member being slidably received about said support member;

said sleeve being movable relative to said support member and said needle to a first position with said needle slidably supported within said front and rear bearing members and with said pointed forward end retracted within said sleeve, a second position with said pointed forward end and a substantial portion of said needle protruding from said sleeve in an outboard direction beyond said front bearing member, and a third position with said pointed forward end retracted through and derailed from said front bearing member;

means for substantially closing said port in said front bearing member when said needle is derailed therefrom to substantially prevent reinsertion therethrough; and indicia means for visibly indicating movement of said sleeve to said third position.

19. The needle safety device of claim 18 further including means for releasably locking said sleeve with respect to said support means in said first and second positions.

20. The needle safety device of claim 19 further including means for locking said sleeve in said third position.

21. The needle safety device of claim 18 wherein said closing means comprises at least one flap disposed generally adjacent said port in said front bearing member, said flap being normally biased for substantially closing said port.

22. The needle safety device of claim 19 wherein said locking means comprises detent members interacting between said sleeve and said support member.

23. A needle safety device for use in combination with a medical needle having a pointed forward end, and a support member supporting said needle to protrude forwardly therefrom, said safety device comprising:

an elongated, generally tubular protective sleeve;

means for mounting said protective sleeve for longitudinally sliding motion about said support member and said needle, said mounting means including front and rear bearing members on said sleeve, said front bearing member having a narrow port formed therein for sliding reception about said needle, and said rear bearing member being slidably received about said support member;

said sleeve being movable relative to said support member and said needle to a first position with said needle slidably supported within said front and rear bearing members and with said pointed forward end retracted within said sleeve, a second position with said pointed forward end and a substantial portion of said needle protruding from said sleeve in an outboard direction beyond said front bearing member, and a third position with said pointed forward end retracted through and derailed from said front bearing member; and indicia means for visibly indicating movement of said sleeve to said third position.

24. The needle safety device of claim 23 wherein said front bearing member includes a generally annular recess formed about said port and presented generally in an axially inboard direction.

* * * * *